United States Patent
Hahn

(10) Patent No.: US 9,592,502 B2
(45) Date of Patent: Mar. 14, 2017

(54) MICROFLUIDIC DEVICE UNIT

(71) Applicant: Buerkert Werke GmbH, Ingelfingen (DE)

(72) Inventor: Thomas Hahn, Kuenzelsau (DE)

(73) Assignee: Bürkert Werke GmbH, Ingelfingen (DE)

( * ) Notice: Subject to any disclaimer, the term of this patent is extended or adjusted under 35 U.S.C. 154(b) by 186 days.

(21) Appl. No.: 14/517,481

(22) Filed: Oct. 17, 2014

(65) Prior Publication Data

US 2015/0118110 A1 Apr. 30, 2015

(30) Foreign Application Priority Data

Oct. 25, 2013 (DE) .................. 10 2013 111 778

(51) Int. Cl.
| | |
|---|---|
| *B01L 3/00* | (2006.01) |
| *G01N 1/28* | (2006.01) |
| *G01N 35/00* | (2006.01) |
| *G01N 35/10* | (2006.01) |

(52) U.S. Cl.
CPC ... *B01L 3/502715* (2013.01); *B01L 3/502723* (2013.01); *G01N 35/0098* (2013.01); *G01N 35/1016* (2013.01); *B01L 3/50273* (2013.01); *B01L 2200/027* (2013.01); *B01L 2200/028* (2013.01); *B01L 2200/10* (2013.01); *B01L 2300/044* (2013.01); *B01L 2300/0672* (2013.01); *B01L 2300/0816* (2013.01); *B01L 2300/0883* (2013.01); *B01L 2300/123* (2013.01); *B01L 2300/1805* (2013.01);
(Continued)

(58) Field of Classification Search
CPC ......... B01L 2200/027; B01L 2200/028; B01L 2300/044; B01L 2300/0672; B01L 2300/0816; B01L 2300/0883; B01L 2300/123; B01L 2300/1805; B01L 3/502715; B01L 3/502723; G01N 2035/00237
See application file for complete search history.

(56) References Cited

U.S. PATENT DOCUMENTS

| | | | |
|---|---|---|---|
| 2002/0124645 A1* | 9/2002 | Wright ................ | G01F 23/18 73/290 V |
| 2003/0049174 A1* | 3/2003 | Ganesan ........... | B01L 3/502715 422/82.02 |

(Continued)

FOREIGN PATENT DOCUMENTS

| | | |
|---|---|---|
| DE | 102006014845 A1 | 10/2007 |
| DE | 202013103016 U1 | 7/2013 |

(Continued)

OTHER PUBLICATIONS

German Search Report issued on Feb. 10, 2014, citing the above reference(s).

*Primary Examiner* — Jennifer Wecker
(74) *Attorney, Agent, or Firm* — Haumptman Ham, LLP

(57) ABSTRACT

A microfluidic device unit has a control device which includes at least one actuating unit and with a carrier for a microfluidic chip. The carrier is designed as module separate from the control device, but is connected with the same by at least one connecting line such that the actuating unit can actuate at least one function at the carrier. The carrier is provided with a receptacle for the microfluidic chip.

14 Claims, 26 Drawing Sheets

(52) U.S. Cl.
CPC .............. *G01N 2035/00237* (2013.01); *G01N 2035/00346* (2013.01); *G01N 2035/1034* (2013.01)

(56) References Cited

U.S. PATENT DOCUMENTS

| | | | | |
|---|---|---|---|---|
| 2004/0083799 | A1* | 5/2004 | Markakis | B82Y 35/00 73/105 |
| 2004/0086427 | A1* | 5/2004 | Childers | B01L 3/502707 422/400 |
| 2006/0275852 | A1* | 12/2006 | Montagu | B01L 3/502715 435/7.93 |
| 2008/0152543 | A1* | 6/2008 | Karaki | B01L 3/5027 422/82.08 |
| 2008/0219890 | A1* | 9/2008 | Lawson | B01L 3/502715 422/81 |
| 2010/0015011 | A1* | 1/2010 | Nemoto | A61M 39/10 422/400 |
| 2013/0193003 | A1* | 8/2013 | Reed | B01L 3/502707 205/775 |
| 2013/0210682 | A1* | 8/2013 | Eltoukhy | B01L 3/502715 506/38 |
| 2014/0076057 | A1* | 3/2014 | Slakhorst | G01L 19/145 73/715 |
| 2014/0335527 | A1* | 11/2014 | Goel | B01L 3/502738 435/6.12 |

FOREIGN PATENT DOCUMENTS

| | | | |
|---|---|---|---|
| EP | 1705488 | A2 | 9/2006 |
| EP | 1721669 | B1 | 9/2011 |
| WO | 2008039875 | A1 | 4/2008 |

\* cited by examiner

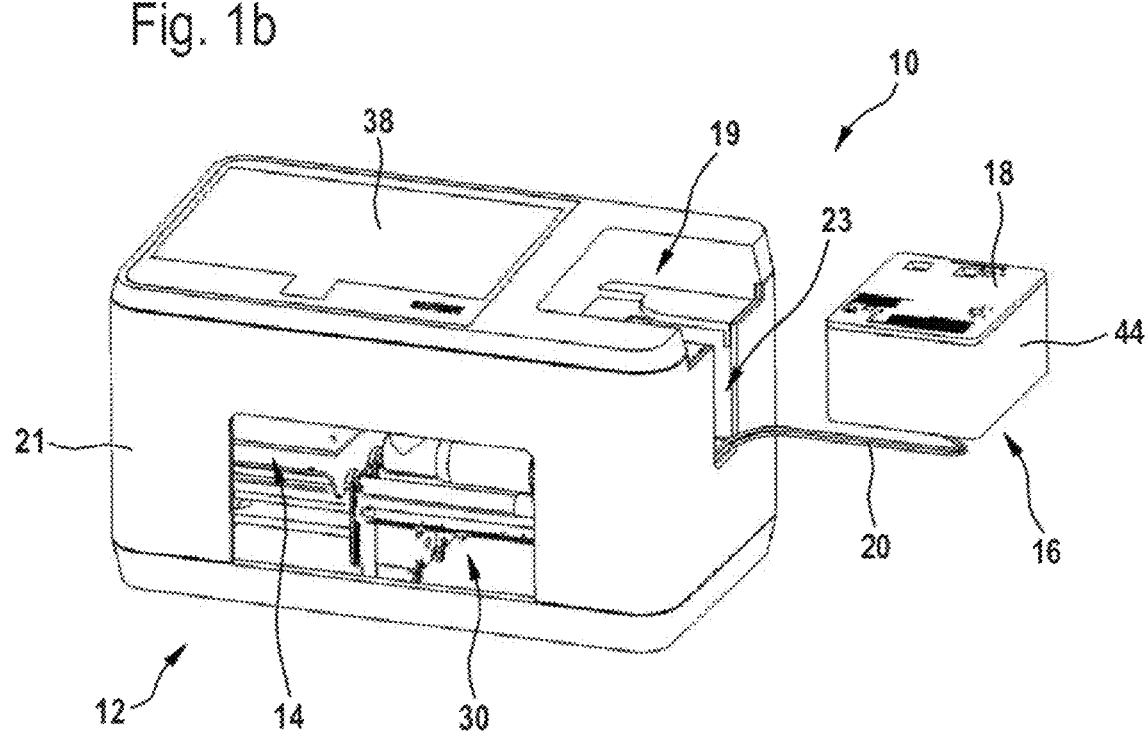

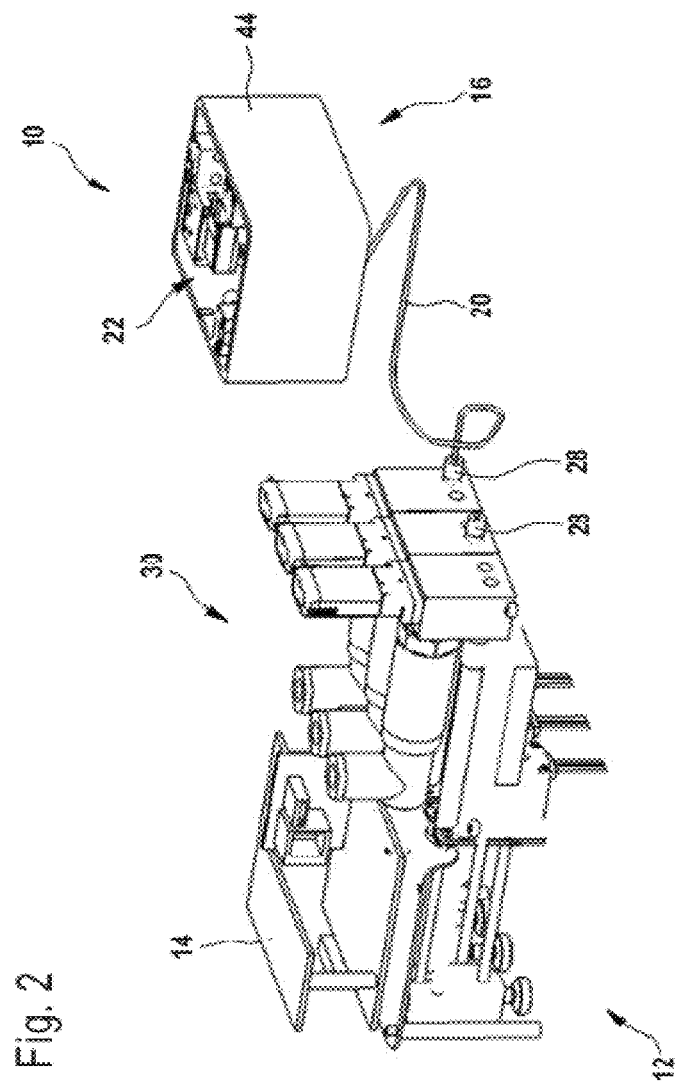

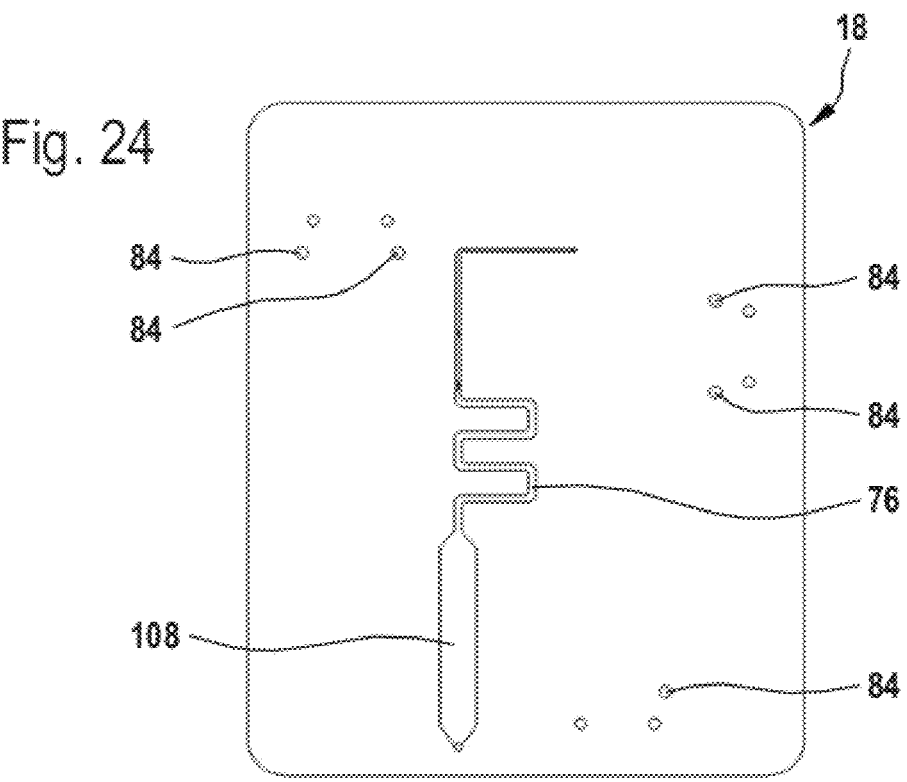

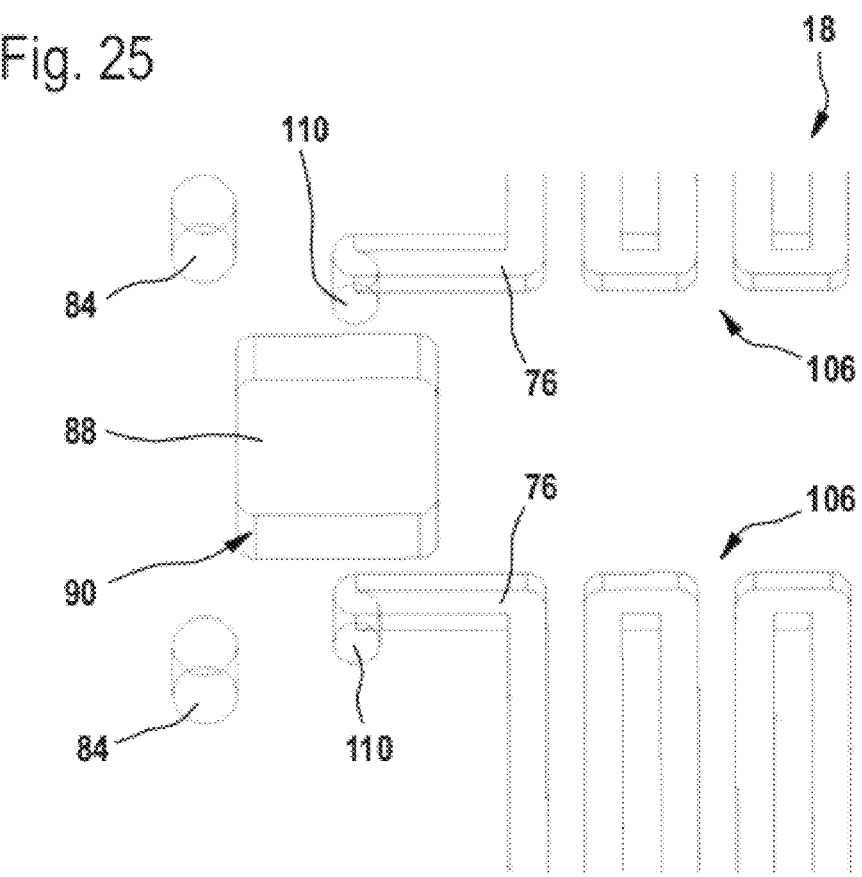

MICROFLUIDIC DEVICE UNIT

CROSS REFERENCE TO RELATED APPLICATION

This application claims the priority of German Patent Application No. 10 2013 111 778.3, filed on Oct. 25, 2013 in the German Patent and Trade Mark Office, the disclosure of which is incorporated herein in its entirety by reference.

This invention relates to a microfluidic device unit with a control device and a carrier for a microfluidic chip.

BACKGROUND OF THE INVENTION

So-called microfluidic chips are already generally known from the prior art and include at least one storage portion, at least one microfluidic channel and mostly at least one mixing portion, in order to examine for example a flow behavior, a mixing and/or demixing behavior as well as chemical and/or biochemical reactions of fluid samples present in the storage portion. For this purpose, the microfluidic chips are inserted into a microfluidic device unit, wherein this device unit comprises at least one actuating unit which charges the fluid samples in the desired way, for example with a compressive force, magnetic force, chemical reaction force, electrical force and/or thermal load.

In U.S. Pat. No. 8,309,040 B2 such microfluidic device unit, a microfluidic chip for accommodation in this device unit, and a method for mounting the microfluidic chip at the device unit are already described. The microfluidic device unit includes a needle which on insertion of the microfluidic chip penetrates into the sealed storage portion of the microfluidic chip and hence in a simple way creates a largely leakage-free fluid connection between the microfluidic chip and the device unit. The microfluidic chip can be inserted into the microfluidic device unit and again be removed from the device unit with little effort, so that a simple exchange of the microfluidic chips is possible.

It is the object of the invention to create a microfluidic device unit as well as a microfluidic chip, with which the analysis possibilities for a fluid sample are improved.

BRIEF DESCRIPTION OF THE INVENTION

In order to achieve the object, a microfluidic device unit with a control device is provided which includes at least one actuating unit and with a carrier for a microfluidic chip. The carrier is designed as module separate from the control device, but is connected with the same by at least one connecting line such that the actuating unit can actuate at least one function at the carrier: The carrier is provided with a receptacle for the microfluidic chip. The design as module separate from the control device provides for a "freer" handling of the carrier and hence improved analysis possibilities for the microfluidic chip mounted at the carrier. For example, the mobile carrier module along with the mounted microfluidic chip can be put onto a microscope and the microfluidic chip can be examined in the mounted condition. During this examination, the at least one connecting line at the same time provides for an actuation of the microfluidic chip via the control device.

In one embodiment of the microfluidic device unit, the carrier includes at least one light source which can be actuated from the actuating unit via the connecting line. The microfluidic chip and hence the fluid sample thereby can be irradiated with light in a simple way.

Furthermore, the carrier can include at least one light sensor whose signals can be transmitted to the actuating unit via the connecting line. The connecting line thus not only provides for the transmission of actuating signals from the control device to the microfluidic chip, but in addition also for the transmission of feedback signals from the microfluidic chip to the control device.

In a further embodiment of the microfluidic device unit, the carrier includes at least one heating element which is connected with the actuating unit via the connecting line. In this way, the microfluidic chip and hence the fluid sample can be heated with little effort.

Preferably, the heating element is mounted at the carrier in an elastically yielding manner. In the mounted condition of the microfluidic chip this leads to a pretension and hence to a close contact between the heating element and the region of the microfluidic chip to be heated, so that a heat transfer is ensured with little loss of energy.

In a further embodiment of the device unit, the carrier includes an induction element which can be actuated by the actuating unit via the supply line. In this way, the application of an electric and/or electromagnetic force onto the fluid sample in the microfluidic chip or also the transmission of energy to a heating means arranged in the microfluidic chip becomes possible with little effort.

At the carrier of the microfluidic device unit there is preferably arranged an arresting means for a microfluidic chip. Such arresting means reliably fixes the microfluidic chip at the carrier and for example prevents undesired slipping of the microfluidic chip, when the carrier along with the microfluidic chip is inserted into a microscope.

The arresting means particularly preferably includes a permanent magnet or a counterpart of a magnetic material. A magnetic arresting means offers the advantage that microfluidic chips in this way can easily and repeatably both be fixed at the carrier and again be removed from the carrier.

According to a further embodiment of the device unit, a fluidic coupling for automatically connecting a microfluidic chip is integrated into the receptacle of the carrier. Via this fluidic coupling, a hydraulic or pneumatic force can be applied onto the fluid sample in the microfluidic chip.

Preferably, the fluidic coupling contains at least one hollow needle. By inserting and withdrawing a hollow needle, the fluidic coupling can be produced or released with minimum effort. In addition, by inserting the hollow needle, possibly supported by a simple sealing ring, a tightness of the fluidic connection is achieved.

The hollow needle in particular is replaceably mounted at the receptacle. This offers the advantage that a clogged or damaged hollow needle can be replaced very easily and quickly.

Particularly preferably, the fluidic coupling includes at least one hollow supply needle and at least one hollow discharge needle. Thus, the microfluidic chip on the one hand can take up a working medium for pressurizing the fluid sample via the hollow supply needle and on the other hand provide for venting via the hollow discharge needle. Sample fluid and/or working medium possibly can also be discharged to the control device of the microfluidic device unit via the carrier. An additional reservoir for sample fluid and/or working medium in the microfluidic chip is not required then.

In a further embodiment of the device unit, the control device includes at least one pump which can be actuated by the actuating unit and whose output is connected with the carrier via the connecting line. The pump for pressurizing the fluid sample thus is located outside the mobile carrier, so that the same can be designed in a particularly compact form and for example can be put under a microscope together with the microfluidic chip.

In this embodiment of the device unit the pump preferably is connected with the fluidic coupling. This provides for an easy pressurization of the fluid sample via the pump in the control device. By means of the pressurization, one or more fluid samples or a fluid sample and a reagent, which initially are kept in stock in separate channel structure portions in the microfluidic chip, are transported to a reaction space or a mixing portion, where for example by means of optical components an analysis of the fluidic components is performed.

In a further embodiment of the device unit the receptacle for the microfluidic chip consists of several pedestals. This support of the microfluidic chip on individual pedestals at least sectionally provides for a free geometric design of the microfluidic chip and the carrier as well as for a good accessibility of the microfluidic chip for examining the fluid sample.

In this embodiment, preferably at least one of the pedestals is provided with the fluidic coupling.

This pedestal then preferably is provided with a port for a fluid line which is connected with the pump.

In addition, at least one of the pedestals can be provided with a light source and/or a light sensor. In this way it is possible with little technical effort to optically examine the fluid sample or to also examine its behavior during an irradiation with light. Furthermore, the concentration of a constituent in a fluid sample can be determined or constituents of a fluid sample can be analyzed.

Furthermore, at least one of the pedestals can be provided with a permanent magnet or a counterpart of a magnetic material. With a suitable design of the microfluidic chip this provides for an easy magnetic fixation or arrestment of the microfluidic chip at the carrier and in addition also for an easy disassembly of the microfluidic chip by selectively overcoming the magnetic holding force. The microfluidic chip includes a base body which is made of a moldable plastic material and in which at least one microfluidic channel is provided, which is open towards at least one of the side faces of the base body, and with a sealing film which fully extends over the side faces of the base body on which the microfluidic channel is open. The base body preferably is provided with at least one coupling surface for light. Via the carrier of the microfluidic device unit, this coupling surface for light provides for a selective irradiation of the fluid sample with light and for a good detection of a reflection from the fluid sample.

Preferably, the coupling surface is a side wall of a depression which extends from one of the side faces of the base body.

This coupling surface for example can extend at an angle of about 45° to the side face. In the case of an irradiation vertical to the side face of the microfluidic chip, the light thus can be deflected in a direction parallel to the side face, so that an advantageous irradiation of the fluid sample is possible. This applies analogously to a light sensor which is oriented vertically to the side face and via the coupling surface beveled at an angle of 45° for example can detect a transmission radiation directed parallel to the side face.

The side wall of the depression, which is formed as coupling surface, for example is part of a pyramid. Above all, this offers manufacturing benefits during the production of the base body for the microfluidic chip.

In addition, the side wall of the depression in particular can be coated with a reflective material, in order to improve the light reflection.

In one embodiment of the microfluidic chip the base body is flat and includes two side faces extending parallel to each other, which are rectangular and face away from each other.

The two side faces in particular are provided with a sealing film. This construction provides for an easy and inexpensive manufacture of the microfluidic chip.

The microfluidic channel of the microfluidic chip preferably includes at least one storage portion. This storage portion contains a reagent or the fluid sample during the storage of the microfluidic chip, i.e. before the microfluidic chip is mounted on the carrier of the device unit and examined.

In addition, the microfluidic channel can include at least one mixing portion. In this mixing portion, different fluid samples for example are combined and analyzed by means of a pressurization of the microfluidic chip.

In one embodiment of the microfluidic chip the base body is an injection-compression-molded part of a transparent thermoplastic material such as polycarbonate or polymethyl methacrylate (PMMA).

Particularly preferably, the base body of the microfluidic chip is provided with a permanent magnet or a counterpart of a magnetic material. With a suitable design of the carrier, this provides for an easy positioning or arrestment of the microfluidic chip on the carrier of the microfluidic device unit. It thereby is ensured that the microfluidic chip mounted on the carrier does not slip or fall down in an undesired way during a movement of the mobile carrier.

BRIEF DESCRIPTION OF THE DRAWINGS

Further features and advantages of the invention can be taken from the following description of preferred embodiments with reference to the drawings, in which:

FIGS. 1a and 1b show perspective views of a microfluidic device unit according to the invention with control device and carrier as well as a microfluidic chip mounted on the carrier;

FIG. 2 shows a further perspective view of the microfluidic device unit according to FIGS. 1a and 1b, but without housing of the control device and without microfluidic chip;

FIG. 24 shows a bottom view of the microfluidic chip according to FIGS. 21 to 23; and FIG. 25 shows a detailed view of the microfluidic chip in the connecting region for a fluidic coupling of the carrier.

DETAILED DESCRIPTION OF THE INVENTION

Figure 3:
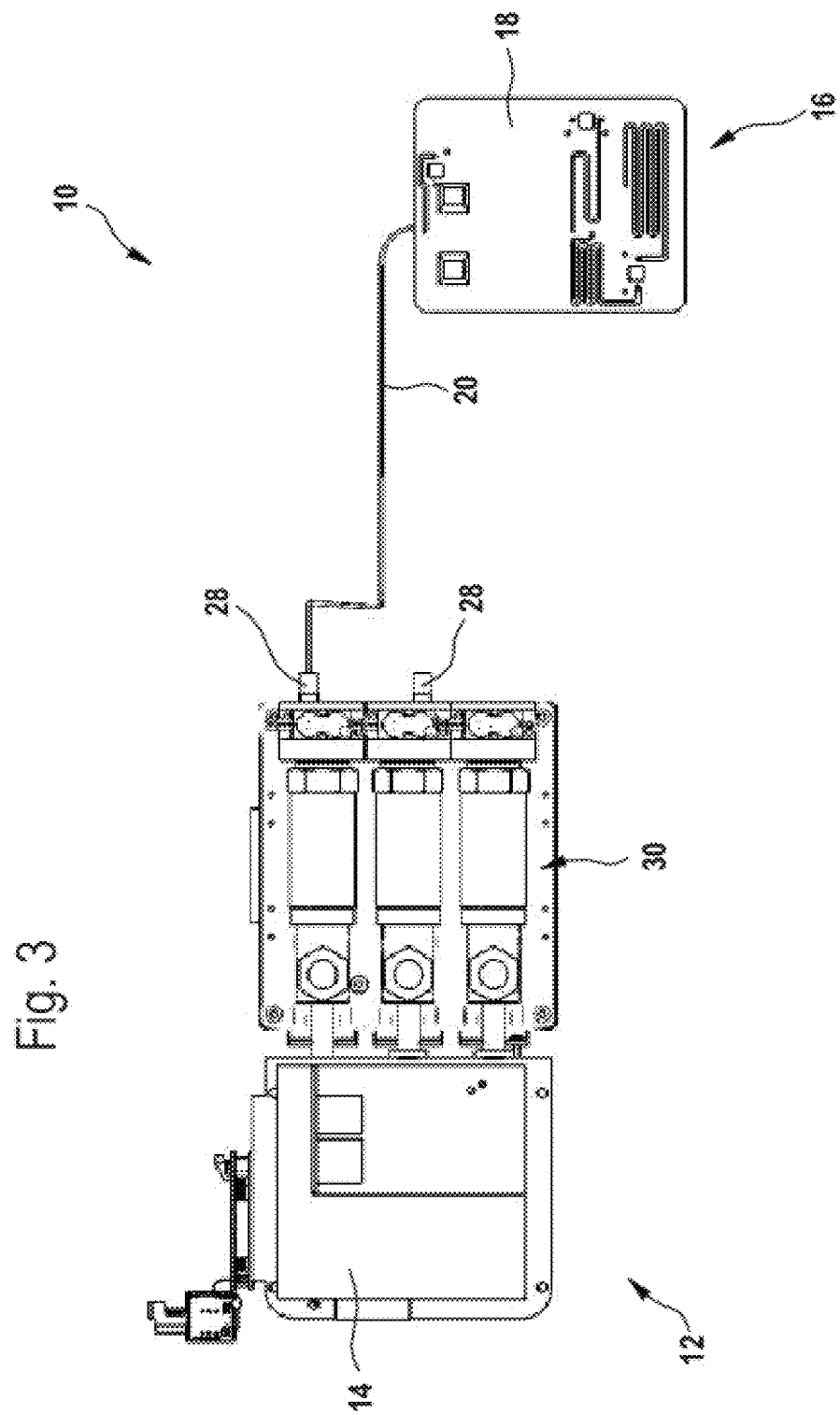
FIG. 3 shows a top view of the microfluidic device unit according to FIG. 2 with mounted microfluidic chip.

FIGS. 1 to 3 shows a microfluidic device unit 10 with a control device 12, which includes at least one actuating unit 14, and a carrier 16 for a microfluidic chip 18.

The carrier 16 is designed as module separate from the control device 12, but connected with the same by at least one connecting line 20 such that the actuating unit 14 can actuate at least one function at the carrier 16.

Usually, there are provided several connecting lines 20, for example fluid lines, power lines or other signal lines, which for better handling of the carrier 16 preferably are combined to one line bundle.

Figure 1A:
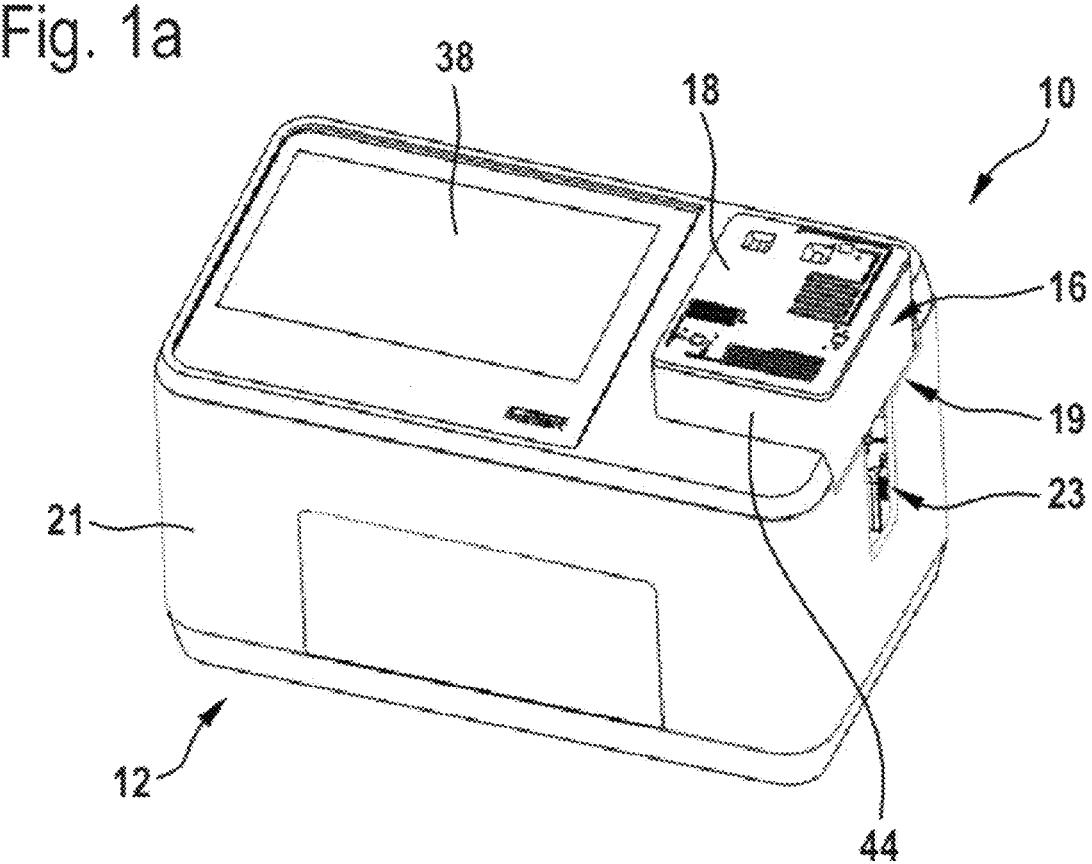

In a first operating condition of the microfluidic device unit 10 according to FIG. 1a, the carrier 16 is inserted into the control device 12, so that the carrier 16 together with the control device 12 forms a uniform and compact assembly which substantially is formed cuboid. In the control device 12 a precision-fit recess 19 is provided for accommodating the carrier 16. According to FIG. 1a, the carrier 16 slightly protrudes with respect to the control device 12, but in an alternative design variant also can terminate substantially flush with a housing 21 of the control device 12 and form a uniform surface with the control device 12.

FIG. 1b shows a second operating condition of the microfluidic device unit 10, in which the carrier 16 is removed from the recess 19 of the control device 12, but nevertheless always remains connected with the control device 12 via the connecting line 20. To facilitate the removal of the carrier 16, a cutout 23 adjoining the recess 19 is provided in the control device 12, which in the first operating condition of the microfluidic device unit 10 is arranged below the carrier 16, so that the carrier 16 can laterally be grasped by hand and can easily be removed from the control device 12.

The carrier 16 is provided with a receptacle 22 for the microfluidic chip 18, wherein in FIGS. 1a, 1b and 3 a microfluidic chip 18 already is mounted on the carrier 16 of the microfluidic device unit 10.

Into the receptacle 22 of the carrier 16 a fluidic coupling 24 is integrated for automatically connecting the microfluidic chip 18, whose exact configuration will be discussed in more detail in the description of FIGS. 17 and 18.

Figure 17:
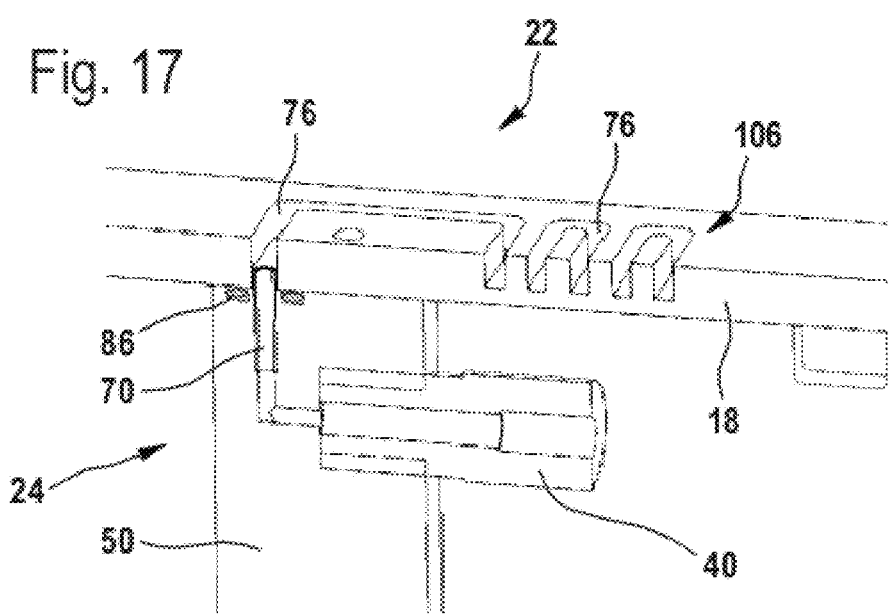
FIG. 17 shows a perspective detail section of the carrier with mounted microfluidic chip in the region of the pedestal according to FIG. 15.
Figure 18:
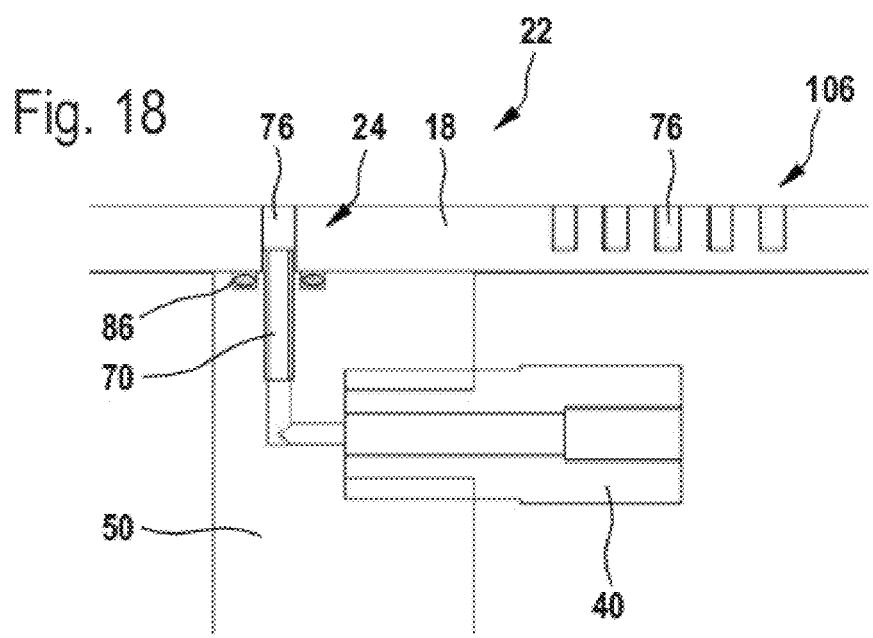
FIG. 18 shows a side view of the carrier with mounted microfluidic chip according to FIG. 17.

According to FIGS. 1 to 3, the control device 12 of the microfluidic device unit 10 includes a pump unit 30 with several pumps 26 which can be actuated by the actuating unit 14 and whose outputs 28 are in fluid connection with the carrier 16 of the microfluidic device unit 10, concretely with the fluidic coupling 24 of the carrier 16, via the at least one connecting line 20 (see also FIGS. 17 and 18).

Figure 4:
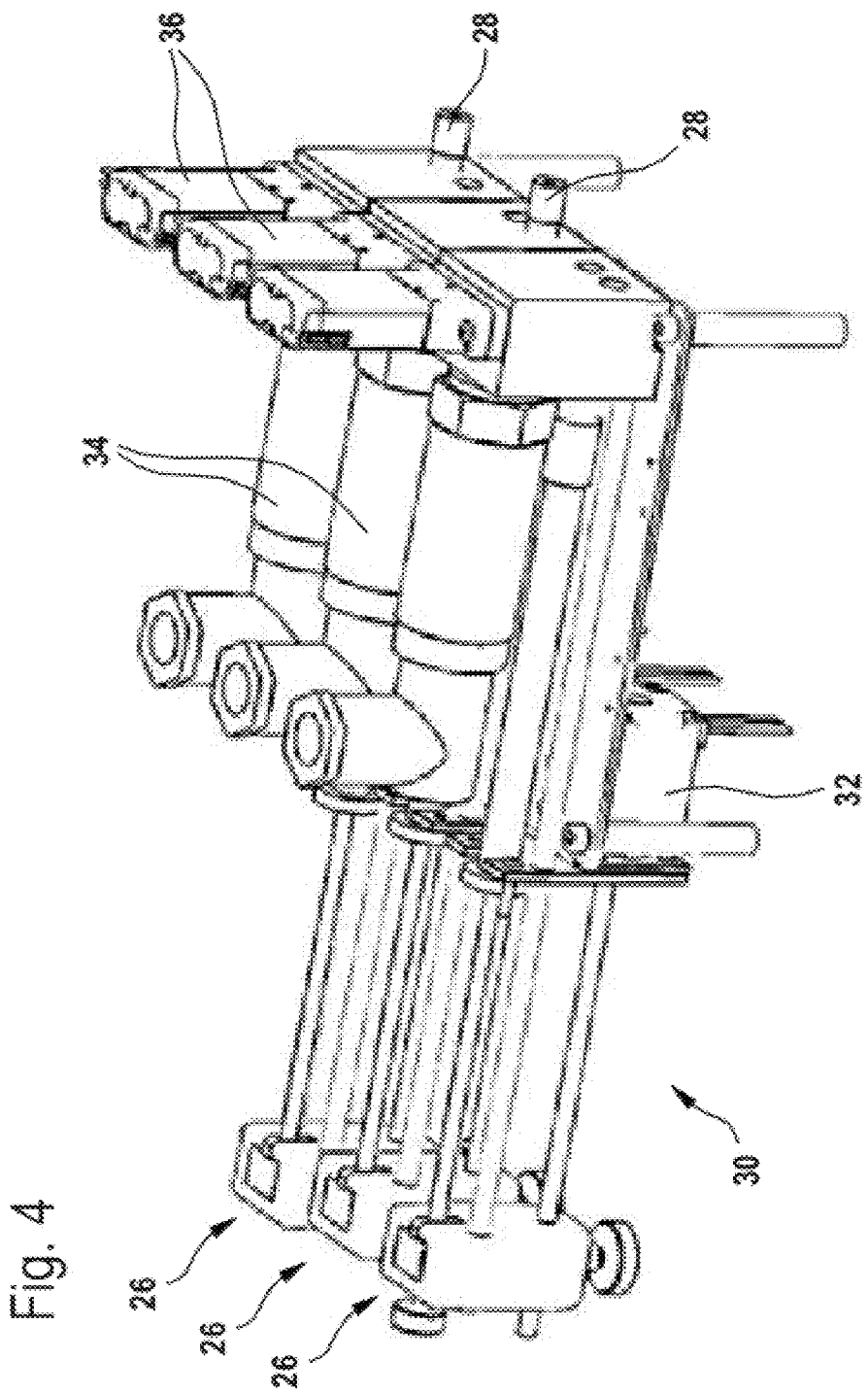
FIG. 4 shows a perspective view of a pump unit in the control device of the microfluidic device unit according to FIGS. 1 to 3.

FIG. 4 shows details of the pump unit 30 of the control device 12, wherein the pump unit 30 here comprises three syringe pumps for providing a working medium. As working medium in particular air is used, wherein alternatively another gas or gas mixture or a liquid can be used. The pump unit 30 is equipped with linear actuators 32 formed as step motors, with pressure transmitters 34 and with valves 36. A fluid sample in the microfluidic chip 18 hence can be conveyed continuously and substantially free from pulsations. The actuation of the pump unit 30 is effected via the actuating unit 14, which in turn is operated via a display 38.

Figure 5:
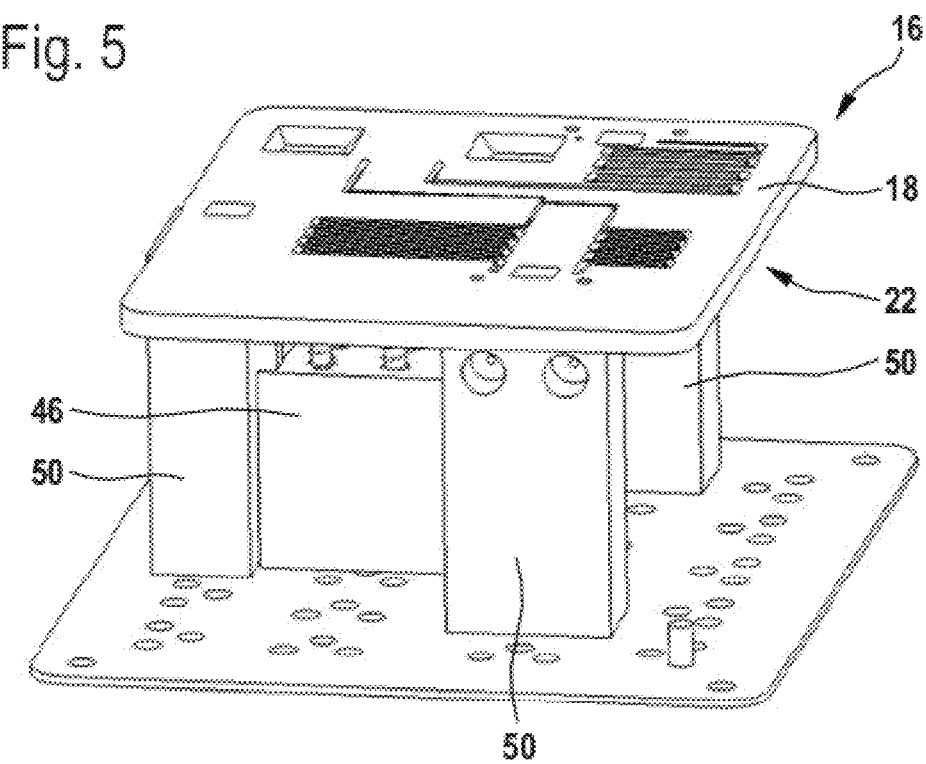
FIG. 5 shows a perspective view of a carrier of the microfluidic device unit without carrier housing, but with mounted microfluidic chip.

FIG. 5 shows the mobile carrier 16 of the microfluidic device unit 10 with a mounted microfluidic chip 18, but without the carrier housing 44. It hence can clearly be seen that the receptacle 22 of the carrier 16 for the microfluidic chip 18 consists of several pedestals 50. In particular, three pedestals 50 are provided, in order to ensure a stable, statically determinate support for the microfluidic chip 18.

Figure 6:
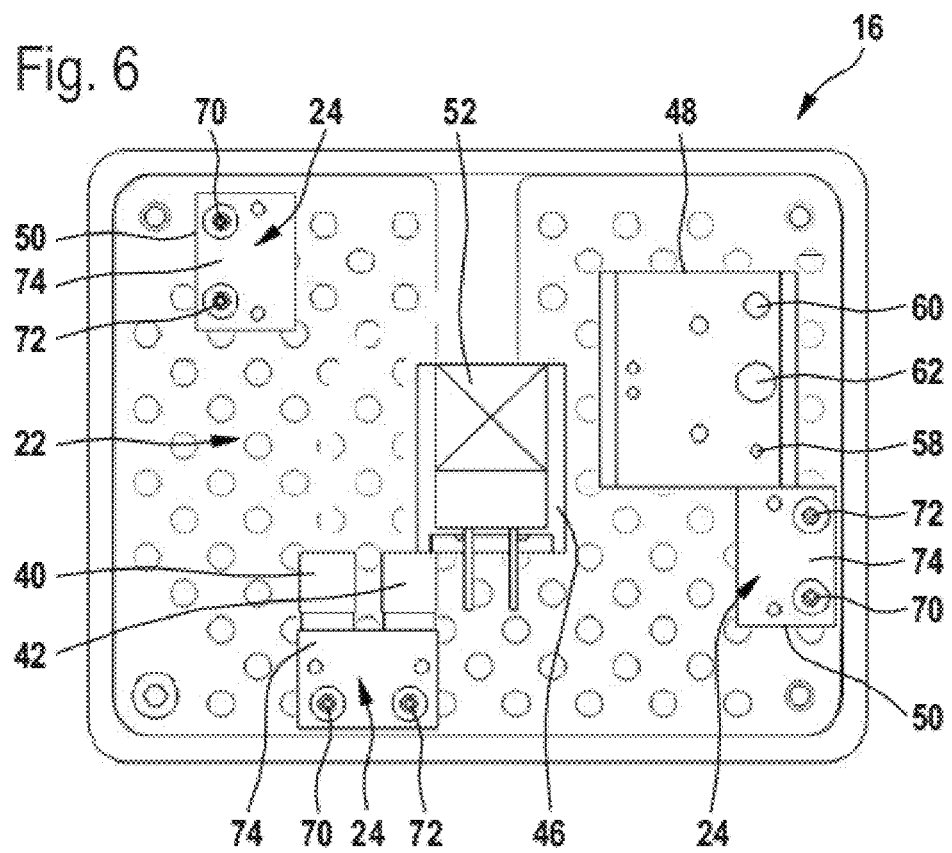
FIG. 6 shows a top view of a carrier of the microfluidic device unit.

FIG. 6 shows a top view of the carrier 16 with the carrier housing 44, but without the microfluidic chip 18. This top view clearly shows that the pedestals 50 are provided with the fluidic coupling 24. Correspondingly, each pedestal 50 also is provided with fluid ports 40, 42 which can be connected with the control device 12, in particular with the pump unit 30 of the control device 12, via the connecting line 20.

Moreover, the carrier 16, concretely a pedestal 46 of the carrier 16, includes a heating element 52 which likewise is connected with the actuating unit 14 of the control device 12 via the connecting line 20. In particular, the heating element 52 is mounted on the carrier 16 in an elastically yielding manner, so that during assembly of the microfluidic chip 18 a certain pressing force is obtained between the microfluidic chip 18 and the heating element 52. This pressing force ensures a good heat transfer to the microfluidic chip 18 whose fluid sample 66 can at least partly be heated by the heating element 52.

According to FIG. 6, the carrier 16 of the microfluidic device unit 10 furthermore includes a pedestal 48 which is provided with a light source 54 and a light sensor 56.

Figure 7:
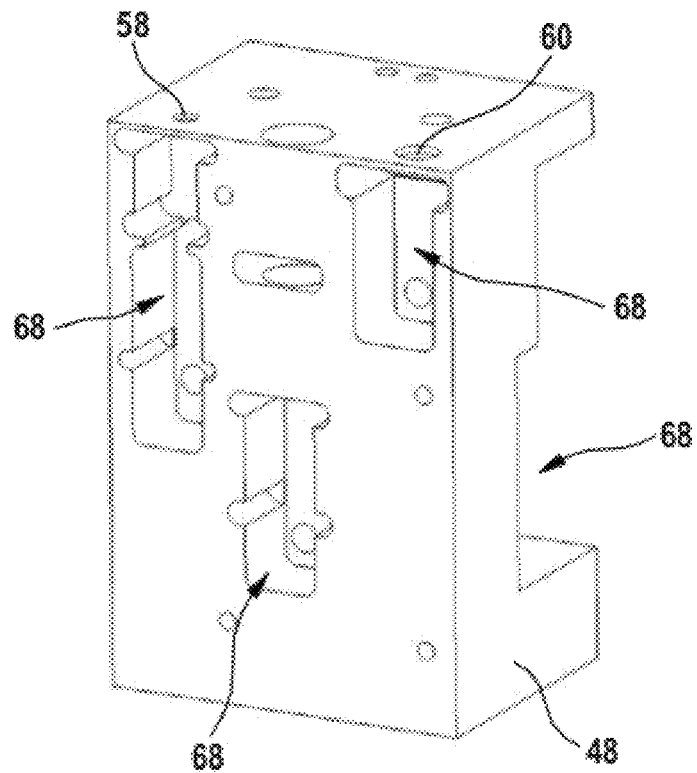
FIG. 7 shows a perspective view of a pedestal for accommodating optical and/or electronic components for the carrier according to FIG. 6.
Figure 8:
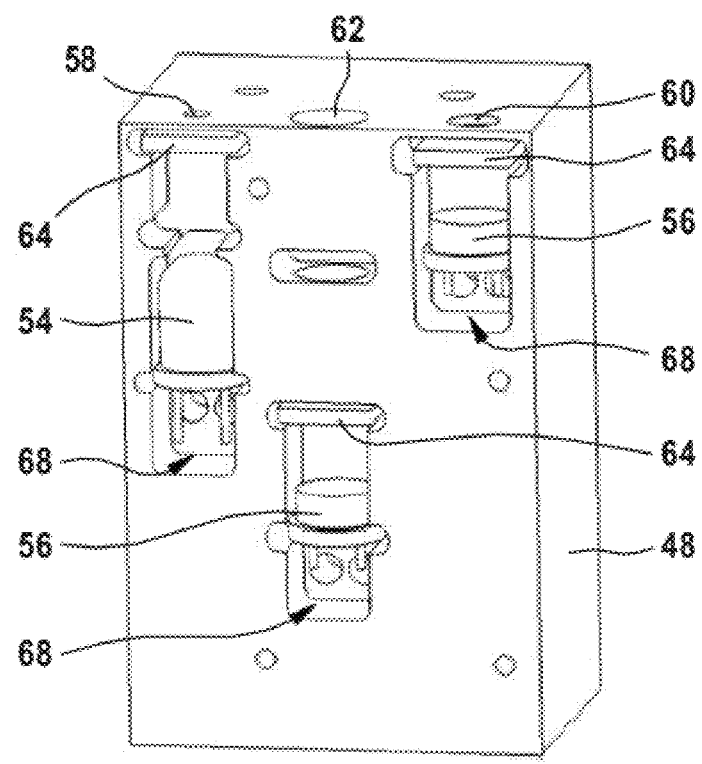
FIG. 8 shows a perspective view of the pedestal according to FIG. 7 with mounted optical and electronic components.

FIGS. 7 and 8 show perspective views of the pedestal 48 without and with optical and electronic fittings. To reduce the manufacturing effort, it is conceivable to form the pedestal 48 for different series of the microfluidic device unit 10 identical in construction, i.e. to generally provide cutouts 68 for conceivable optical and electronic components, which then can optionally be equipped as required.

According to FIG. 8, the pedestal 48 of the carrier 16 includes two orifice plates 58, 60, a light source 54 as well as light sensors 56 for fluorescence and transmission measurement. The light source 54 for example is a light emitting diode and can be actuated from the actuating unit 14 via the connecting line 20. Correspondingly, the light sensors 56 for example are photodiodes whose signals can be transmitted to the actuating unit 14 via the connecting line 20. In addition, optical components for light refraction and frequency filtration also are incorporated into the pedestal 48, such as for example a lens 62 or chromatic filters 64. The device unit 10 furthermore comprises an electronic evaluation unit for detecting the optical signals, so that the fluid samples and their constituents can be analyzed.

Figure 9:
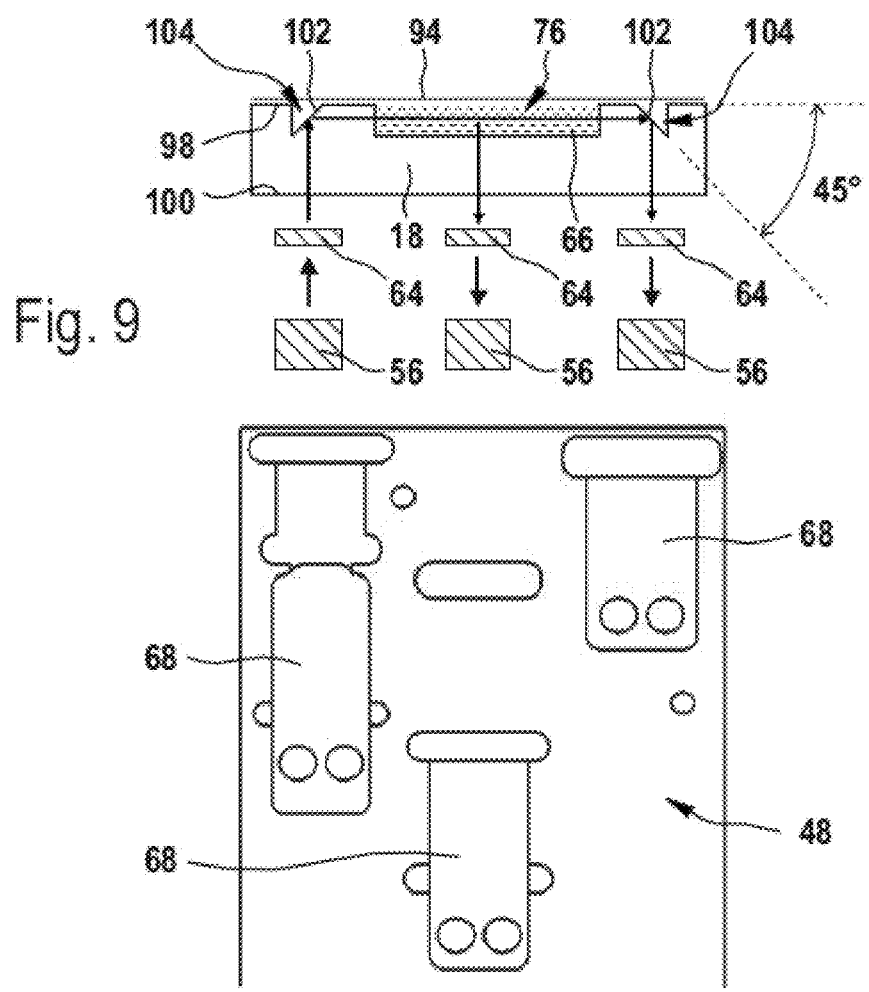
FIG. 9 shows a view of the pedestal according to FIG. 7 as well as a schematic diagram for explaining the optical principle.

In the schematic diagram according to FIG. 9 the optical principle for irradiating a fluid sample 66 in the microfluidic chip 18 is shown for the pedestal 48 described above. The light from the light source 54 is introduced into the microfluidic chip 18 via the filter 64, in order to irradiate the fluid sample 66 with light and subsequently be able to carry out fluorescence and/or transmission measurements via suitable light sensors 56.

The conduction of light in the microfluidic chip 18 will yet be discussed in detail in the detailed description of the microfluidic chip 18 with reference to FIGS. 21 to 25.

Figure 10:
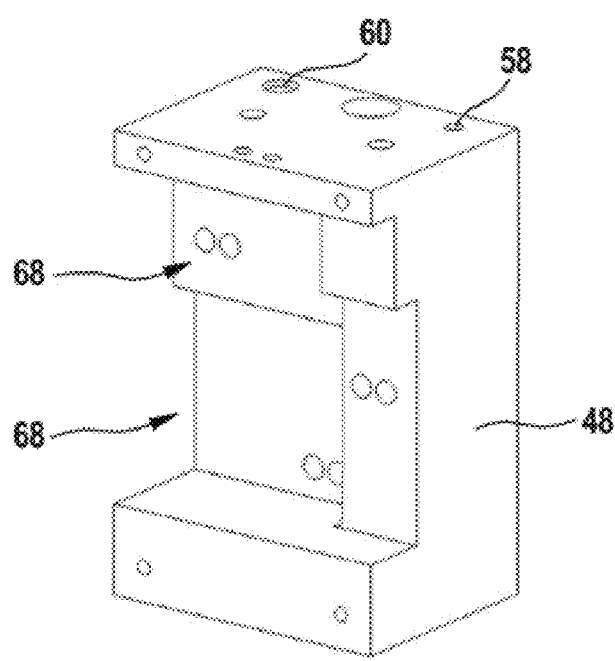
FIG. 10 shows a further perspective view of the pedestal according to FIG. 7.
Figure 11:
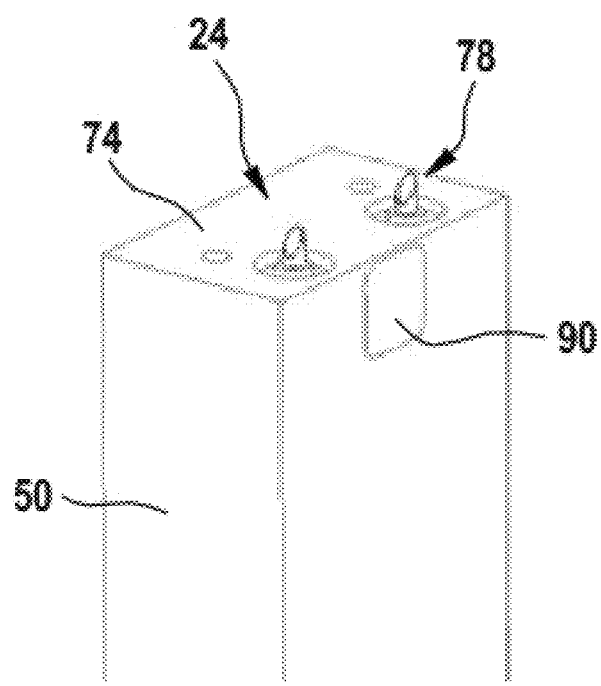
FIG. 11 shows a perspective view of a further pedestal for the carrier according to FIG. 6.
Figure 12:
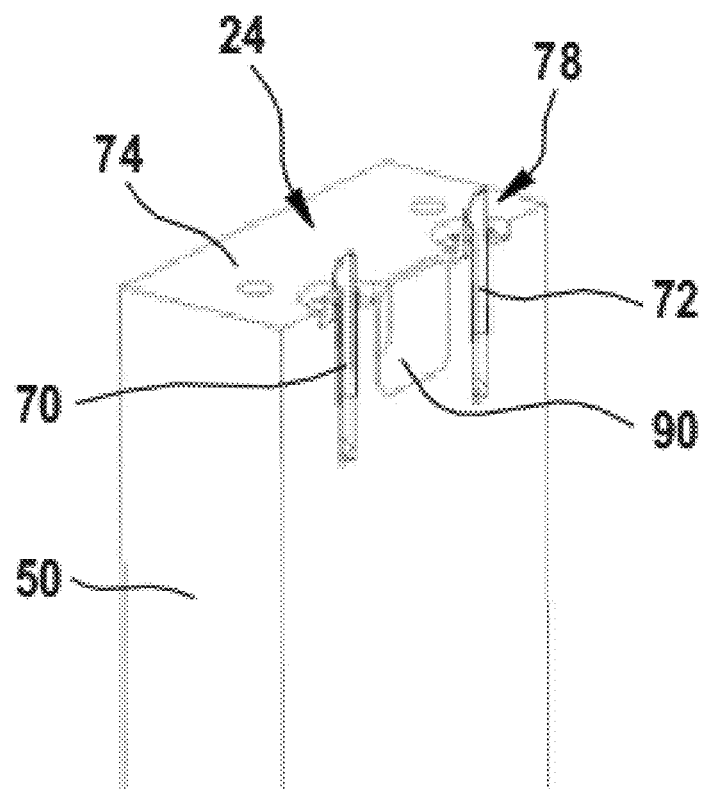
FIG. 12 shows a perspective sectional view of the pedestal according to FIG. 11.
Figure 13:
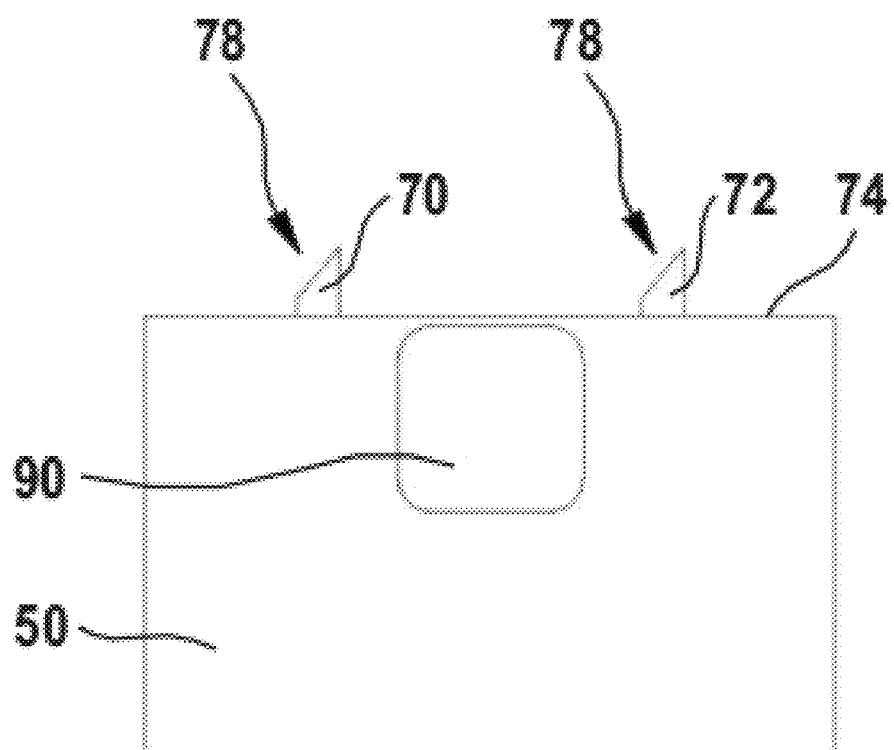
FIG. 13 shows a side view of the pedestal according to FIG. 11.
Figure 14:
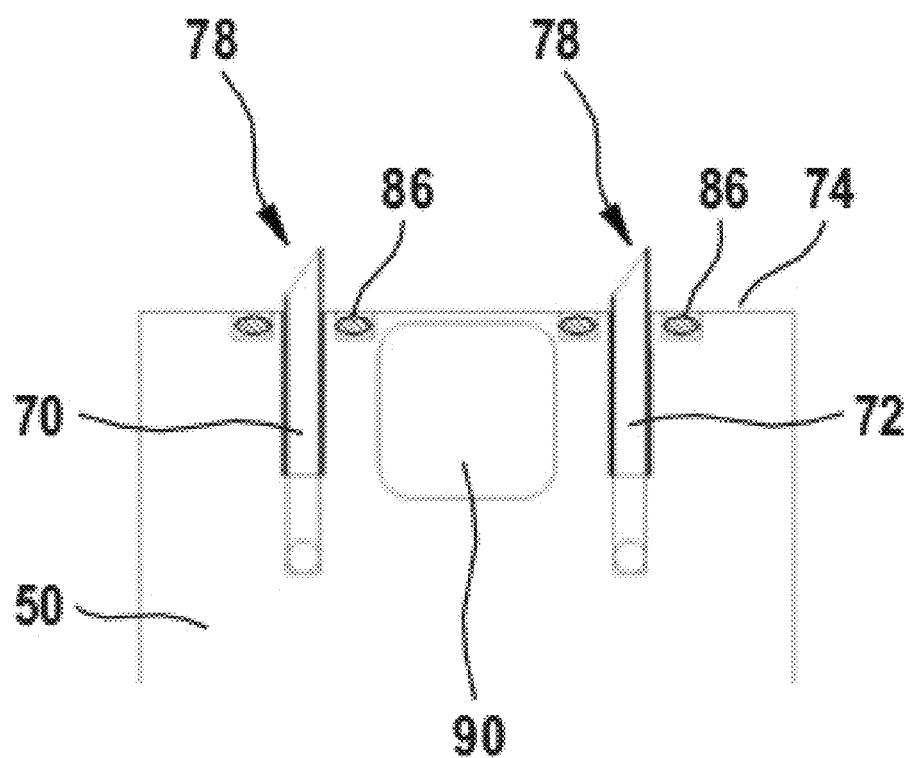
FIG. 14 shows a side view of the pedestal according to FIG. 12.

FIG. 10 shows the pedestal 48 according to FIGS. 7 and 8 in a perspective rear view in which further cutouts 68 for electronic components can be seen. Examples for electronic components, which can be accommodated in these cutouts 68, include an electronic board for actuating the light source 54 or an amplifier for evaluating the light sensors 56.

Of course it is possible to integrate further functions into the pedestals 46, 48, 50 of the carrier 16 or to provide additional pedestals with further functions. It is conceivable, for example, that the carrier 16 includes an induction element (not shown) which via the connecting line 20 can be actuated by the actuating unit 14, in order to apply an electric or electromagnetic force onto the fluid sample 66.

FIGS. 11 to 16 show possible detail configurations of the fluidic coupling 24 which is integrated into the receptacle 22 of the carrier 16.

The fluidic coupling 24 each contains two hollow needles 70, 72 which are replaceably mounted at the receptacle 22 of the carrier 16. One of the hollow needles 70, 72 is a hollow supply needle 70 for feeding working medium from the control device 12 into the microfluidic chip 18, whereas the other one of the hollow needles 70, 72 is a hollow discharge needle 72 which substantially serves for venting. It might additionally be provided that via the hollow discharge needle 72 sample fluid and/or working medium is discharged from the microfluidic chip 18 to the control device 12.

The hollow needles 70, 72 protrude beyond a bearing surface 74 of the pedestal 50, so that during assembly of the microfluidic chip 18 they penetrate into a microfluidic channel 76 of the microfluidic chip 18 (see FIGS. 17 and 18).

A first design variant of the fluidic coupling 24, in which the hollow needles 70, 72 have beveled ends 78, is shown in FIGS. 11 to 14. The sharp-edged beveled ends 78 of the hollow needles 70, 72, which protrude beyond the bearing surface 74, offer the advantage that the fluid connection to the microfluidic channels 76 of the microfluidic chip 18 can be accomplished with minimum expenditure of force. For this reason, however, particular care must be taken when positioning and mounting the microfluidic chip 18 at the receptacle 22 of the carrier 16, so that the microfluidic chip 18 is not damaged by the beveled ends 78 of the hollow needles 70, 72 already before reaching its final mounting position.

Figure 15:
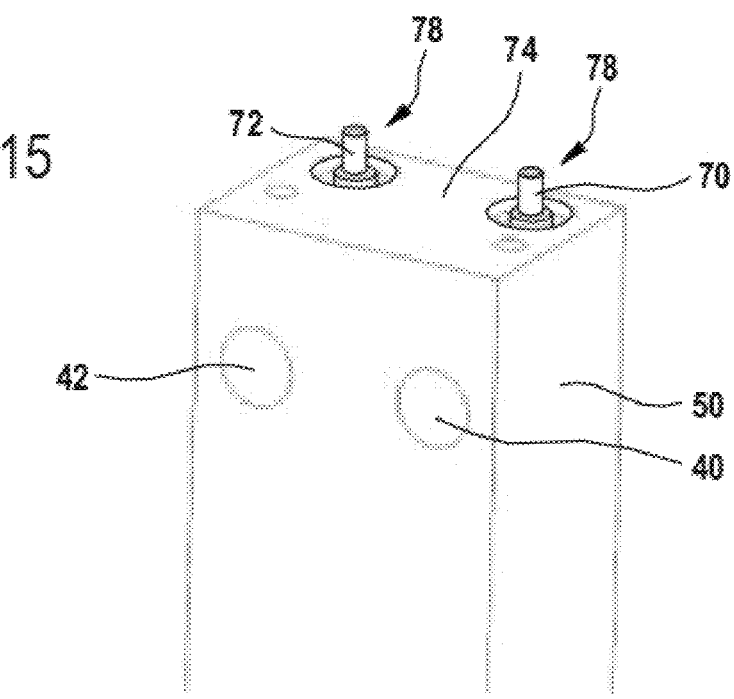
FIG. 15 shows a perspective view of the pedestal according to FIG. 11 in an alternative embodiment.

In an alternative, second design variant of the fluidic coupling 24 according to FIG. 15, the ends 78 of the hollow needles 70, 72 are flattened and extend parallel to the bearing surface 74 of the pedestal 50. In this design variant, the risk of the microfluidic chip 18 being damaged before reaching its final mounting position is reduced distinctly. However, as compared to the first design variant according to FIGS. 11 to 14, a distinctly higher mounting force is necessary, in order to connect the fluid ports 40, 42 of the pedestal 50 with the microfluidic channels 76 of the microfluidic chip 18.

Figure 16:
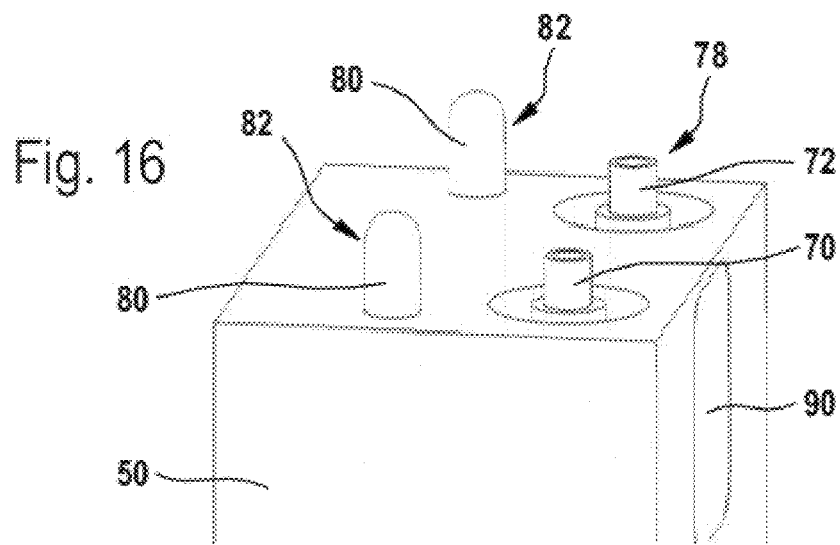
FIG. 16 shows a perspective view of the pedestal according to FIG. 11 in a further alternative embodiment.

In an alternative, third design variant of the fluidic coupling 24 according to FIG. 16 positioning pins 80 are provided, which protrude beyond the bearing surface 74 of the pedestal 50, in order to further reduce the risk of the microfluidic chip 18 being damaged before reaching its mounting position. Preferably, the positioning pins 80 protrude more beyond the bearing surface 74 of the pedestal 50 than the ends 78 of the hollow needles 70, 72. Moreover, the free ends 82 of the positioning pins 80 are rounded or flattened, so that a damage of the microfluidic chip 18 before reaching its mounting position largely is excluded. On reaching the mounting position, the positioning pins 80 engage into corresponding positioning openings 84 of the microfluidic chip 18 (see FIGS. 24 and 25). By applying a corresponding mounting force vertical to the bearing surface 74, the connection to the microfluidic channels 76 of the microfluidic chip 18 then can be accomplished in the mounting position.

Preferably, the available magnetic force is sufficiently large, so that when placing the microfluidic chip 18 on the positioning pins 80, the microfluidic chip 18 is attracted by the magnetic force until reaching its stable mounting position at the bearing surface 74, wherein the ends of the hollow needles 70, 72 then pierce the sealing film 96. There is not required an additional pressing force applied from outside.

The fluid connection between the fluid port 40 of the carrier 16 and the microfluidic channel 76 of the microfluidic chip 18 is shown in the detail sections of FIGS. 17 and 18. The fluid port 40 is formed at the pedestal 50 of the carrier 16 and is in fluid connection with a replaceable hollow needle 70, wherein in the mounted condition of the microfluidic chip 18 the hollow needle 70 protrudes into its microfluidic channel 76 and hence is fluidically connected with the microfluidic chip 18.

In general, the pump unit 30 thus is in flow connection with the fluidic coupling 24 of the carrier 16 via the output 28, the connecting line 20 and the fluid port 40.

According to FIGS. 17 and 18 a sealing ring 86 is provided in the bearing surface 74 of the pedestal 50, which encloses the hollow needle 70 and seals the puncture point towards the microfluidic chip 18.

Particularly preferably, an arresting means 88 for the microfluidic chip 18 is arranged at the carrier 16, in order to prevent undesired slipping of the mounted microfluidic chip 18 during a movement of the mobile carrier 16. The arresting means 88 in particular includes a permanent magnet or a counterpart of a magnetic material. In the illustrated exemplary embodiments at least one of the pedestals 50 of the carrier 16 concretely is provided with such arresting means 88. Corresponding cutouts 90 for accommodating the arresting means 88 already are indicated in FIGS. 11 to 14 and 16, wherein the cutouts 90 are arranged close to the bearing surface 74 in the pedestal 50.

When a permanent magnet or a counterpart of a magnetic material is used as arresting means 88 in the pedestal 50, a counterpart of a magnetic material or a permanent magnet correspondingly must be provided as arresting means 88 in the microfluidic chip 18, in particular in a base body 92 of the microfluidic chip 18. In this connection, FIG. 19 shows the carrier 16 of the microfluidic device unit 10 with mounted microfluidic chip 18, wherein the microfluidic chip 18 for example includes three magnetic arresting means 88.

Figure 19:
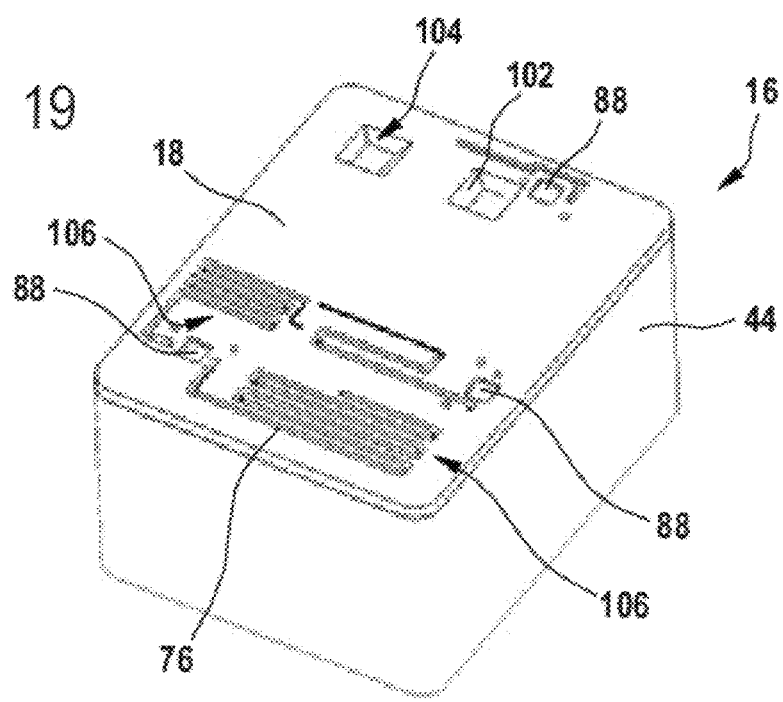
FIG. 19 shows a perspective view of the carrier of the microfluidic device unit according to the invention with mounted microfluidic chip.
Figure 20:
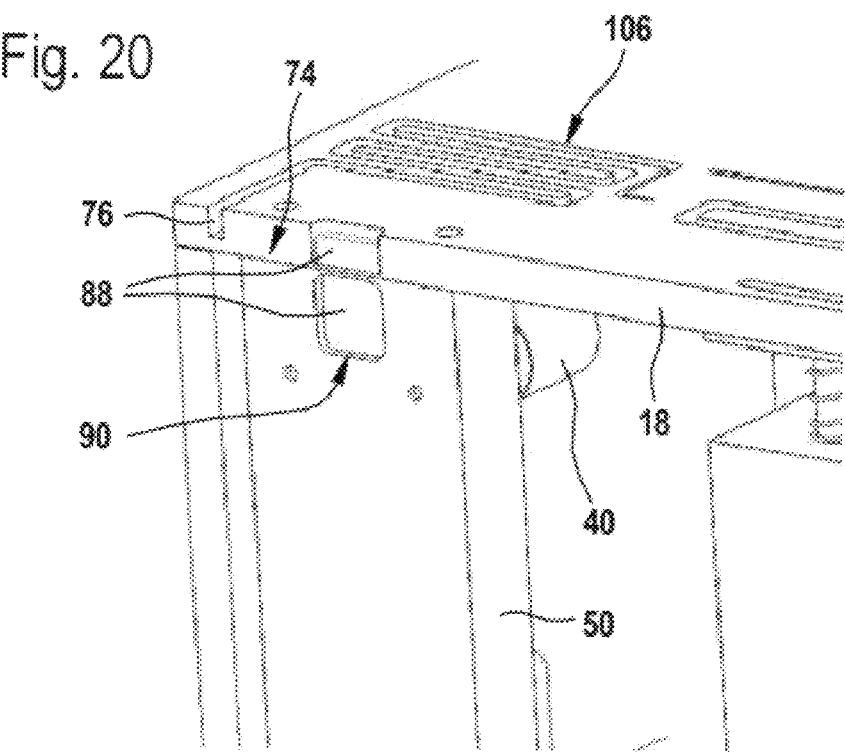
FIG. 20 shows a perspective detail section through the carrier with mounted microfluidic chip according to FIG. 19 in the region of an arresting means.

FIG. 20 shows a detail section through the carrier 16 with mounted microfluidic chip 18 according to FIG. 19 in the region of the arresting means 88. It becomes clear that the cooperating magnetic arresting means 88 maximally have approached each other in the mounting condition of the microfluidic chip 18 and hence exert a magnetic force which urges the microfluidic chip 18 into its mounting position.

When for mounting at the carrier 16 the microfluidic chip 18 is placed onto the positioning pins 80 according to FIG. 16 and shifted parallel to the bearing surface 74, the magnetic force of the arresting means 88 in particular is so great that upon reaching the mounting position of the microfluidic chip 18 the magnetic force exceeds the necessary mounting force and correspondingly the hollow needles 70, 72 are pressed into the microfluidic channels 76 of the microfluidic chip 18.

Figure 21:
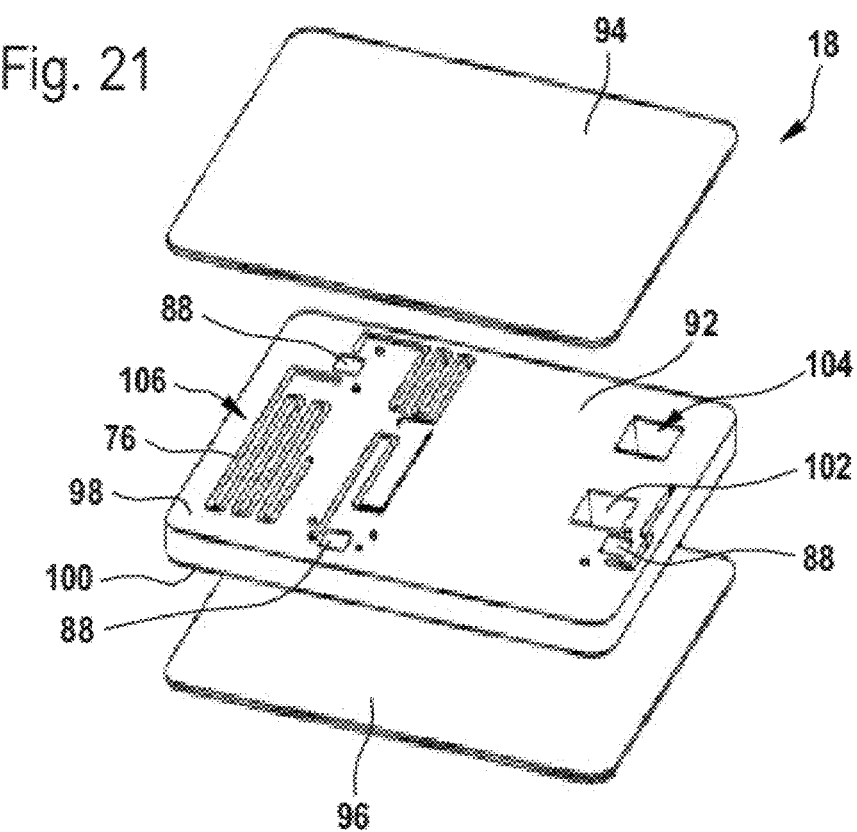
FIG. 21 shows a perspective exploded view of a microfluidic chip according to the invention.

FIG. 21 shows the construction of the microfluidic chip 18 for mounting at the microfluidic device unit 10 according to FIGS. 1 to 20, comprising a base body 92 which is made of a moldable plastic as well as a sealing film 94, 96 which fully extends over the side face 98, 100 of the base body 92. The base body 92 and the sealing films 94, 96 are formed transparent at least in the region of the pedestal 48.

In the base body 92 of the microfluidic chip 18 at least one microfluidic channel 76 is provided, which is open at least on one of the side faces 98, 100 of the base body 92 and is covered and closed by the sealing film 94, 96. In the present case, each of the two opposite side faces 98, 100 of the base body 92 is provided with a sealing film 94, 96.

The base body 92 in particular is a flat injection-compression-molded part of a transparent thermoplastic material such as polycarbonate or PMMA, wherein the two side faces 98, 100 facing away from each other substantially are rectangular and extend parallel to each other.

Due to this construction of the microfluidic chip 18 the material and manufacturing costs are extremely low, so that the microfluidic chip 18 advantageously can be used as disposable part.

Figure 22:
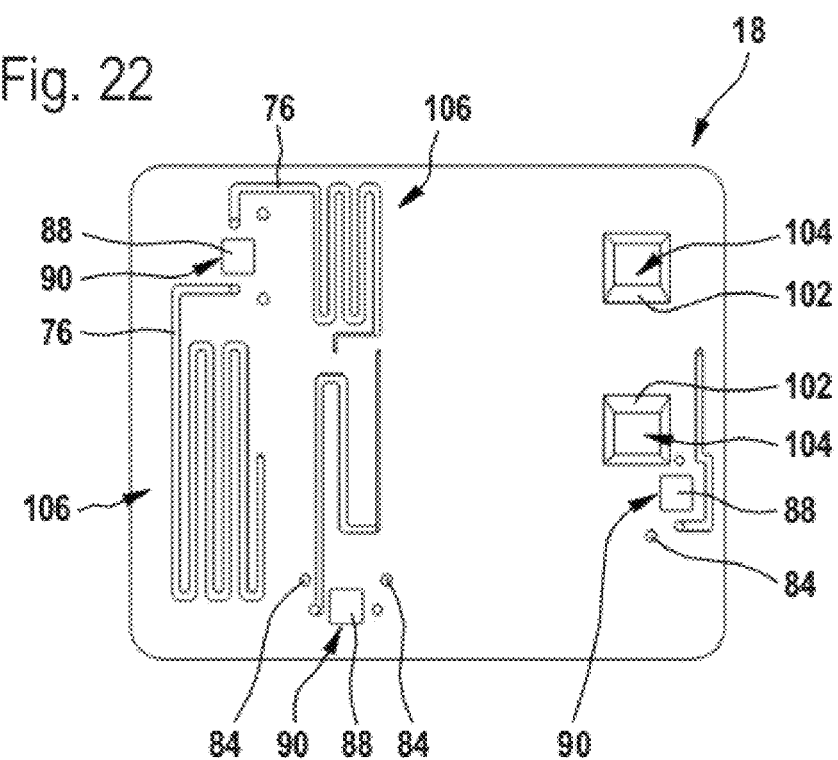
FIG. 22 shows a top view of the microfluidic chip according to FIG. 21.
Figure 23:
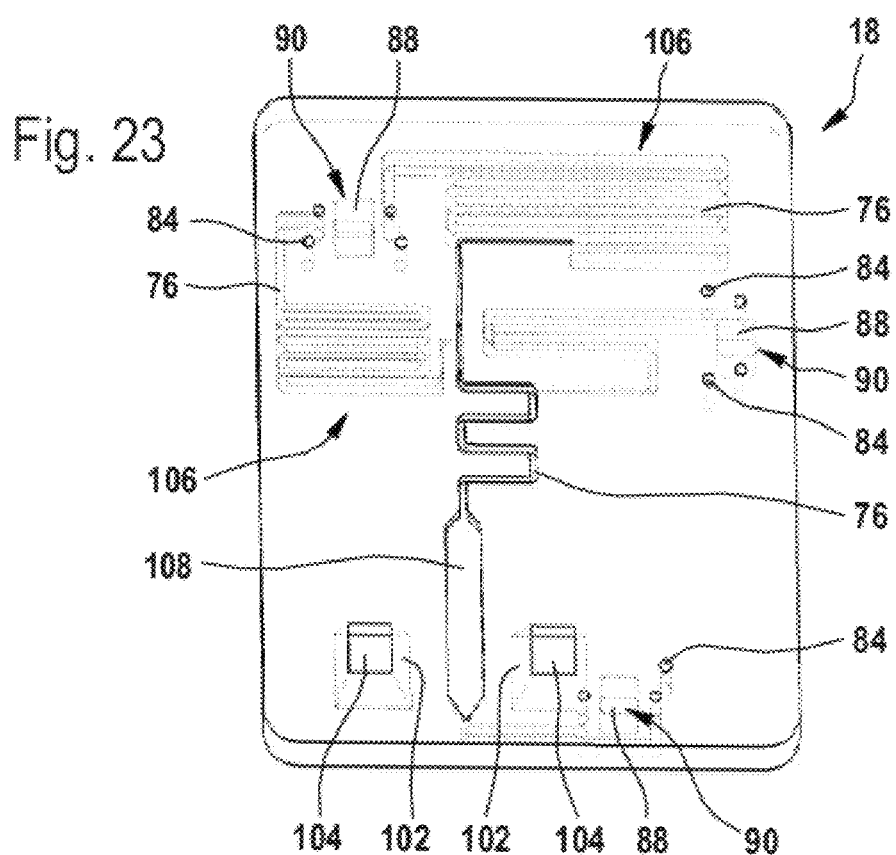
FIG. 23 shows a perspective, partly transparent bottom view of the microfluidic chip according to FIG. 21.

FIG. 22 shows a top view of the microfluidic chip 18 according to FIG. 21, whereas FIG. 23 shows a perspective, partly transparent bottom view and FIG. 24 shows a bottom view of the microfluidic chip 18 according to FIG. 21.

In particular with reference to FIGS. 21 to 23 it becomes clear that the base body 92 is provided with coupling surfaces 102 for light. Each coupling surface 102 is a side wall of a depression 104 which proceeding from one of the side faces 98, 100 extends into the base body 92, wherein the depression 104 in particular is formed like a truncated pyramid and the side wall thus is part of the shell surface of a quadrangular truncated pyramid. However, there can also be used other geometrical figures with only three side faces, for example.

The side wall formed as coupling surface 102 for light in particular can be coated with a reflective material, in order to intensify the light reflexion of the side wall.

Furthermore, the coupling surface 102 for light preferably extends at an angle of about 45° to the side face 98, 100 of the base body 92, as indicated in FIG. 9. At an angle of the coupling surface 102 for light of 45°, light of the light source 54 impinging vertically to the side faces 98, 100 is deflected by the coupling surface 102 such that the fluid sample 66 is irradiated parallel to the side faces 98, 100 of the base body 92. For transmission measurement, the light from a further coupling surface 102 analogously is again deflected in a direction vertical to the side faces 98, 100, so that the light directly impinges on the light sensor 56 in the pedestal 48.

According to FIGS. 21 to 23, the microfluidic channels 76 in the microfluidic chip 18 include two storage portions 106 which serve as reservoir for the fluid sample 66 or a reagent. These storage portions 106 preferably are constructed meander-shaped with at least three channel windings. In this way, with a comparatively small height of the microfluidic chip 18, i.e. a small dimension of the base body 92 vertical to the side faces 98, 100, a relatively large fluid quantity can be stored. The microfluidic chip 18 thus is particularly flat, which has a positive effect on the analysis possibilities and analysis results of the fluid sample 66.

Furthermore, the microfluidic channels 76 of the microfluidic chip 18 according to FIGS. 23 and 24 comprise a mixing portion 108 in which for example an examination or analysis of the fluid sample 66 is made.

FIG. 25 finally shows a part of the microfluidic chip 18 in the connecting region with the fluidic coupling 24 of the carrier 16. There are shown in particular the cutout 90 for accommodating the arresting means 88 and two positioning openings 84 for accommodating positioning pins 80 of the pedestal 50. Furthermore, meander-shaped storage portions 106 of two microfluidic channels 76 are indicated, which at their channel ends each have a connecting region 110 at which hollow needles 70, 72 can penetrate into the microfluidic channel 76, in order to create a fluid connection between the microfluidic channel 76 and the control device 12.

The arrangement of the pedestals 46, 48, 50 in the carrier 16 is adjusted to the geometry of the microfluidic chip 18 and the arrangement of the microfluidic channels 76 such that defined functions automatically are achieved: The pedestals 46, 48, 50 are arranged in the carrier 16 such that on insertion of the microfluidic chip 18 into the receptacle 22 of the carrier 16 the ends 78 of the hollow needles 70, 72 accommodated in the pedestals 50 protrude into the storage portions 106 of the microfluidic channels 76. The pedestal 48 which accommodates the optical components likewise is arranged in the carrier 16 such that on insertion of the microfluidic chip 18 into the receptacle 22 of the carrier 16 an optical measurement path is formed through the mixing portion 108 or a reaction chamber of the microfluidic channels 76.

In the following, the mode of operation of the microfluidic device unit 10 will be explained with reference to an example.

Initially, at least one storage portion 106 of the microfluidic chip 18 is filled with a reagent (or a fluid sample 66). For this purpose the sealing film 94, 96 is pierced, preferably with a syringe, at a point adjacent to the intended puncture point of the hollow needle 70, 72 accommodated in the pedestal 50. As a result, an air cushion remains before the fluid. The reaction chamber or the mixing portion 108 in the same way is filled with the fluid sample 66 to be analyzed by means of a syringe piercing through the sealing film 94, 96. For venting the air in the microfluidic channels 76, additional openings are incorporated into the sealing film 94, 96.

The microfluidic chip 18 thus prepared is inserted into the receptacle 22 of the carrier 16, wherein at least one of the hollow needles 70, 72 accommodated in the pedestals 50 pierces the sealing film 96 below the air cushion and protrudes into the microfluidic channel 76 in the region of the storage portion 106. The air cushion has the advantage that the hollow needle 70, 72 is not contaminated with reagent. Via the control device 12 a pump 26 of the pump unit 30 is activated and a working medium, preferably air, thus is brought into the storage portion 106 through the hollow needle 70, 72. The reagent thereby is transported to the reaction chamber accommodating the fluid sample 66. The reaction chamber is arranged in the microfluidic chip 18 such that in the mounting position of the microfluidic chip 18 it is located between two coupling surfaces 102 for light. By means of the optical components which are accommodated in the pedestal 48 arranged below the reaction chamber an optical measurement path is formed, wherein light traverses the reaction chamber. By means of an electronic evaluation unit in the control device 12 the signals are detected and evaluated, which provides for an analysis of the fluid sample 66. The measurement results are indicated at the display 38 of the control device 12.

With the device unit 12 many analyses can be performed one after the other in a simple way. For this purpose, the microfluidic chips 18 simply are exchanged.

The invention claimed is:

1. A microfluidic device unit, comprising
a control device which includes at least one actuating unit, and comprising
a carrier for a microfluidic chip,
wherein the carrier formed as module separate from the control device, but connected with the same by at least one connecting line configured for allowing the actuating unit to actuate at least one function at the carrier,
wherein the carrier is provided with a receptacle for the microfluidic chip,
wherein the receptacle consists of several pedestals,
wherein a fluidic coupling for automatically connecting the microfluidic chip is integrated into the receptacle,
wherein at least one of the pedestals is provided with the fluidic coupling, and
wherein the pedestal is provided with a port for a fluid line which is connected with a pump.

2. The device unit according to claim 1, wherein the carrier includes at least one light source configured for being be actuated from the actuating unit via the connecting line.

3. The device unit according to claim 1, wherein the carrier includes at least one light sensor whose signals can be transmitted to the actuating unit via the connecting line.

4. The device unit according to claim 1, wherein the carrier includes at least one heating element which is connected with the actuating unit via the connecting line.

5. The device unit according to claim 4, wherein the heating element is mounted on the carrier in an elastically yielding manner.

6. The device unit according to claim 1, wherein the carrier includes an induction element configured for being actuated by the actuating unit via the connecting line.

7. The device unit according to claim 1, wherein an arresting means for the microfluidic chip is arranged at the carrier.

8. The device unit according to claim 7, wherein the arresting means includes a permanent magnet or a counterpart of a magnetic material.

9. The device unit according to claim 1, wherein the fluidic coupling contains at least one hollow needle.

10. The device unit according to claim 9, wherein the hollow needle is replaceably mounted at the receptacle.

11. The device unit according to claim 1, wherein the fluidic coupling includes at least one hollow supply needle and at least one hollow discharge needle.

12. The device unit according to claim 1, wherein the control device includes at least one pump configured for being actuated by the actuating unit and whose output is connected with the carrier via the connecting line.

13. The device unit according to claim 1, wherein at least one of the pedestals is provided with a light source and/or a light sensor.

14. The device unit according to claim 1, wherein at least one of the pedestals is provided with a permanent magnet or a counterpart of a magnetic material.

* * * * *